United States Patent [19]

Miller

[11] 4,387,720
[45] Jun. 14, 1983

[54] TRANSDUCER ACOUSTIC LENS

[75] Inventor: David G. Miller, Andover, Mass.

[73] Assignee: Hewlett-Packard Company, Palo Alto, Calif.

[21] Appl. No.: 221,080

[22] Filed: Dec. 29, 1980

[51] Int. Cl.³ .............................................. A61B 10/00
[52] U.S. Cl. .................................... 128/660; 73/644
[58] Field of Search ............................. 128/660–663; 73/632, 642, 644; 307/334, 335, 336, 338, 340; 367/103, 119, 150, 152, 154; 525/315

[56] References Cited

U.S. PATENT DOCUMENTS

| | | | |
|---|---|---|---|
| 3,256,367 | 6/1966 | Jayne, Jr. | 525/240 |
| 3,387,604 | 6/1968 | Erikson | 73/642 X |
| 3,687,219 | 8/1972 | Langlois | 73/644 X |
| 3,958,559 | 5/1976 | Glenn et al. | 128/660 |
| 4,184,094 | 1/1980 | Kopel | 128/660 X |
| 4,205,686 | 6/1980 | Harris et al. | 128/660 |
| 4,211,948 | 7/1980 | Smith et al. | 128/660 X |
| 4,217,516 | 8/1980 | Iineima et al. | 128/660 X |
| 4,277,712 | 7/1981 | Honafy | 128/660 X |
| 4,296,349 | 10/1981 | Nakanishi et al. | 310/335 |
| 4,325,381 | 4/1982 | Glenn | 128/660 |

FOREIGN PATENT DOCUMENTS 2011219 7/1979 United Kingdom ............... 73/644

OTHER PUBLICATIONS

Wells, P. N. T., *Ultrasonics in Physical Diagnosis,* Churchill Livingstone, N.Y. 1977, pp. 97–112.

Primary Examiner—Lee S. Cohen
Assistant Examiner—Francis J. Jaworski
Attorney, Agent, or Firm—Donald N. Timbie

[57] ABSTRACT

A lens structure is disclosed for a transducer that is utilized to transmit pulses of alternating pressure waves into the body of a patient and produce signals in response to reflections from the body. The lens is comprised of a first lens element having a concave face facing the crystals and a second lens element filling the space between. The acoustic velocity of the first lens element is greater than that of the body and of the second lens element, but the acoustic impedance of the lens elements is similar to that of the body.

5 Claims, 7 Drawing Figures

U.S. Patent  Jun. 14, 1983  4,387,720
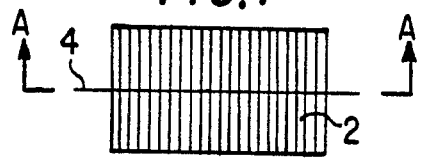
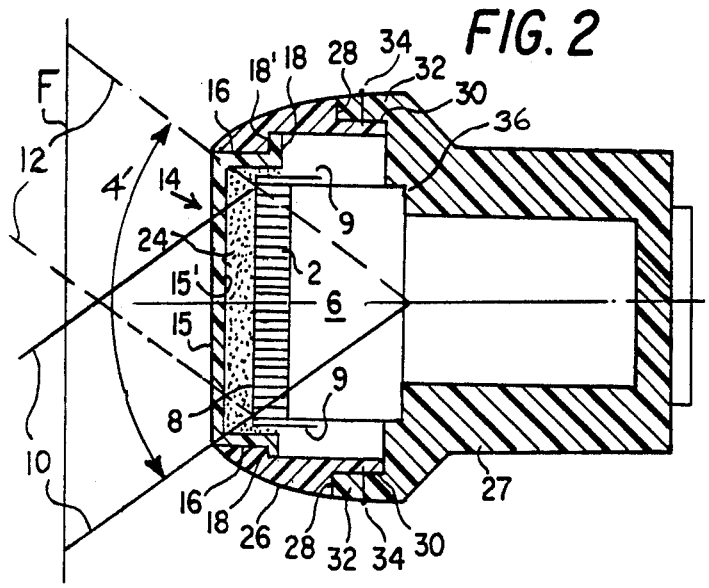
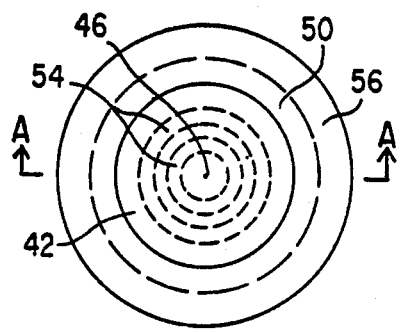
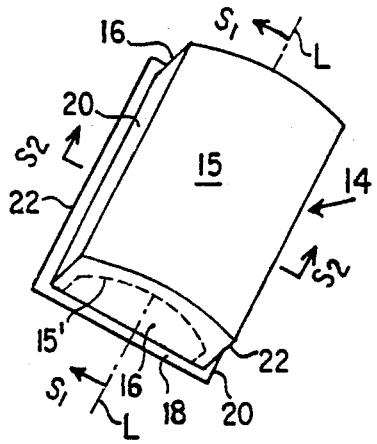
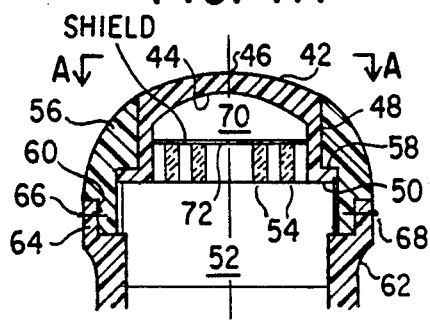
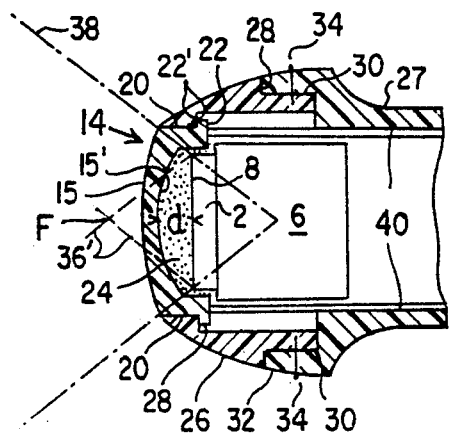
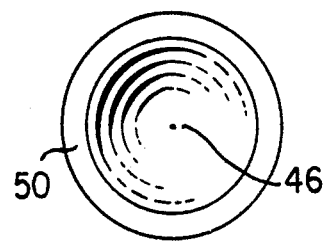

TRANSDUCER ACOUSTIC LENS

BACKGROUND OF THE INVENTION

This invention relates to an improvement in a transducer assembly for transmitting pulses of pressure waves into a body of a patient and/or receiving reflections of portions of the acoustical energy contained in those pulses and producing corresponding electrical pulses that can be used to form an image. A transducer assembly designed for these purposes may be comprised of a linear array of transducer elements, usually piezoelectric crystals, mounted in spaced parallel relationship along a line on an acoustic energy absorbing base with their lengths perpendicular to the line, or it may be comprised of annular piezoelectric crystals mounted in concentric spaced relationship on a base. Ideally, the linear array would transmit a beam of acoustic energy within a plane that is perpendicular to the crystals and the base so as to strike targets within the plane but not above or below it, and the annular array would transmit a beam of acoustic energy only along its axis. While neither ideal can be fully realized, it has been found helpful to focus the acoustic beam. Various means for this purpose have been tried. The faces of the crystals remote from the base have been shaped but this is difficult to do. Single element lenses have been formed with epoxy, styrene or silicone rubber but each has one or more of the following disadvantages: improper acoustic impedance match with the body of the patient, susceptibility to chemical attack, or insufficient strength or hardness to protect the fragile crystals of the array. Unfortunately, materials that provide the best protection do not have the desired acoustic impedance.

SUMMARY OF THE INVENTION

In accordance with this invention, a multi-element lens is provided for focussing the acoustic beam. An outer lens element is comprised of electrically insulating material having an acoustic impedance similar to that of a patient's body and an acoustic velocity greater than that of the body. The lens is shaped with a concave inner surface facing the crystals so that the beam of acoustic energy emanating from the crystals is focussed on the focal line. Suitable materials for the lens element include polymethylpentene, polyethylene and polypropylene, all modified with a rubber modifier such as ethylene propylene, as taught in U.S. Pat. No. 3,256,367. The outer surface of the lens may be slightly curved so as to make it easier to rock the transducer while it is in contact with the body of a patient. An inner lens element is comprised of electrically insulating material such as a urethane potting compound in the space between the inner curved surface of the first lens element and a metal shield in contact with the top of the crystals. The electrically insulating material has an acoustic impedance and propagation velocity similar to those of the body of the patient. The shield is usually grounded so as to protect the patient from electrical shock. The lens provides additional electrical isolation. The outer lens element provides good protection for the crystals, is relatively free from chemical attack and can be made to have an acoustic impedance equal to that of the human body.

BRIEF DESCRIPTION OF THE DRAWINGS

FIG. 1 is a view of the tops of the crystals of a linear array;

FIG. 2 is a cross-section of a transducer having a linear array of crystals and constructed in accordance with this invention. The section is taken at the central plane of the azimuthal sector such as indicated at AA of FIG. 1;

FIG. 2A is a projection view of the outer lens element of FIG. 2;

FIG. 3 is a cross-section of a transducer constructed in accordance with this invention as seen at 90° from the central plane of the azimuthal sector;

FIG. 4 is a top view of a transducer designed for an annular array;

FIG. 4A is a vertical cross-section of FIG. 4; and

FIG. 4B is a bottom view of the outer lens element shown in FIG. 4A.

DETAILED DESCRIPTION OF THE INVENTION

In FIG. 1, the tops of the crystals 2 are seen, as well as the edge view of the central plane 4 of the sector through which the beam may be made to scan by exciting the crystals 2 in appropriate sequences.

In FIG. 2, the crystals 2 are seen in cross-section on a base 6 and are covered by a metal shield 8 having downwardly extending skirts 9 at each end. In the interest of simplicity, no attempt has been made to show the electrical lead providing the usual ground connection for the metal shield 8 or the electrical leads that are connected to each of the crystals 2 in order to excite them in such manner that they vibrate in a direction perpendicular to the base 6. The latter leads would also carry the electrical signals produced by reflected acoustic energy that are used to control the intensity of the image. When the crystals 2 are excited in appropriate sequence, the beam which they form is scanned azimuthally within a sector 4', the central plane of which is positioned as the plane 4 of FIG. 1. The beam scans from a position between solid lines 10 at one side of the sector to a position between dashed lines 12 at the other side of the sector.

An outer lens element 14 is mounted in front of the array of crystals 2. As more clearly seen in FIG. 2A, the lens element 14 is comprised of an outer face 15 which may be flat or slightly curved about an axis L as shown, and an inner face 15' shown in dotted lines that is curved about the axis L so as to focus acoustic waves approaching the inner surface 15' along a line F of FIG. 2. End skirts 16 of the lens element 14 that are perpendicular to the axis L extend downwardly from the inner face 15' and have outwardly extending flanges 18. Side skirts 20, not shown in FIG. 2, that are parallel to the axis L extend downwardly from the face 15' and have outwardly extending flanges 22 that are in the same planes as the flanges 18 and are joined thereto. Thus, a cup of generally cylindrical shape is formed by the inner face 15', the end skirts 16 and the side skirts 20.

As seen in FIG. 2, the outer lens element 14 appears as in section $S_1S_1$ of FIG. 2A. When the outer lens element 14 is assembled, the end skirts 16 closely overlap but do not touch the skirts 9 of the shield 8. An inner lens element 24 between the inner face 15' of the outer lens element 14 and the shield 8 may be formed with a potting compound such as urethane.

FIG. 3 is a section of the transducer that is 90° from the section of FIG. 2 so that one of the crystals 2 appears in side view and the outer lens element 14 appears as in section $S_2S_2$ of FIG. 2A, thus making the curvature of its inner surface 15' apparent. The inner walls of side skirts 20 of the outer lens element 14 closely overlap but do not touch the ends of the crystals 2.

Various housings could be used for the functional components of the transducer, but the one illustrated is comprised of a plastic nose 26 and an interfitting hollow plastic handle 27. The interior of the nose 26 includes a first rectangular opening of such dimension as to closely fit against the end skirts 16 of the outer lens element 14, see FIG. 2, as well as against its side skirts 20 as seen in FIG. 3. The interior of the nose 26 also includes a second and larger rectangular opening that fits closely around the outer edges of the flanges 18, FIG. 2, and the outer edges of the flanges 22, FIG. 3. Due to the different sizes of the rectangular openings, ledges 18' and 22' are formed between them which can fit respectively against the flanges 18 and 22 of the outer lens element 14. The outer surface of the nose 26 flares outwardly so as to maintain a rectangular cross-section and has a right angle ledge formed by a shoulder 28 and a wall 30 extending completely around it. The hollow handle portion 27 is provided with a ridge 32 defining a rectangular opening that fits closely with the wall 30 of the nose 26.

The structure described may be assembled as follows. The outer lens element 14 is dropped into the nose 26 so that the flanges 18 and 22 respectively seat on the ledges 18' and 22'. The lens element 14 is then filled with a suitable potting material such as urethane so as to form the inner lens element 24, and the block 6 with its array 2 of crystals is forced into the potting compound by force exerted on the bottom of the base 6 by shoulders 36, FIG. 2, on the inside of the hollow handle 27. A suitable position is determined when the ridge 32 of the handle 27 seats against the shoulder 28 of the nose 26. As shown in FIG. 2 and FIG. 3, pins 34 are then force-fit into predrilled holes, not shown, that extend through the ridge 32 of the handle 27 into the wall 30 of the nose 26.

By using the lens maker's equation derived from Snell's law, the curvature of the inner surface 15' of the outer lens element 14 may be made such as to cause the beam to focus so as to be between the dashed lines 36' of FIG. 3 rather than lying between the dash-dot lines 38 as would otherwise occur. The focal length is selected to optimize the beam width, as explained in an article entitled "Design of Narrow Beam Width Transducers" by G. Kossoff, which appeared in the June 1963 issue of the *Journal of the Acoustic Society of America*. The focussing action is brought about because the velocity of an acoustic wave travelling within the material of the outer lens element 14 is greater than that of an acoustic wave travelling within the patient or within the inner lens element 24.

One of the advantages of using an outer lens element 14 having an acoustic velocity greater than that of the body of the patient is that reflections of transmitted pulse energy returning to the outer surface 15 of the lens element 14 from points that are angularly displaced from the center line of the scanned sector are suppressed by an effect somewhat similar to total internal reflection phenomenon of optics. When reflections from such angularly displaced points meet the material in the outer lens element 14, they are bent so as to travel a longer path through the outer lens element 14 and are therefore greatly attenuated. Some of the angularly displaced reflected energy is also reflected by the outer lens element 14 back into the body.

Acoustic waves differ from optical waves, however, in that there are two critical angles, one for shear waves and a different one for longitudinal waves. Transmission of the waves through the outer lens element in the shear mode provides and opportunity to further reduce the acceptance angle, i.e., the angle on either side of the beam in azimuth, by corrugating one of the surfaces of the lens element 14 so as to prevent the shear waves from propagating through the high velocity medium or from exiting from it. Such corrugations are not shown however.

The following advantages result from a linear transducer structure constructed as described:

(a) As seen in FIG. 3, it focuses acoustic waves in the elevation plane of the transducer;

(b) It provides an impedance match to the patient's body;

(c) It provides a rugged acoustic window on the transducer;

(d) It provides a shock absorbing layer around the fragile acoustic parts;

(e) It provides electrical insulation (patient isolation) between the transducer excitation and signal ground electrode and the patient;

(f) It seals water, oil and cleaning solvents out of the transducer's acoustic stack and wiring;

(g) Its use of an acoustic absorption layer between the high impedance crystal and the strong reflecting structures in the patient's body cuts down the reverberation between bright structures and the transducer face; and (h) It provides attenuation off axis which may be used to suppress grating lobes and spurious scattered acoustic radiation.

FIGS. 4, 4A and 4B illustrate the application of a compound acoustical lens of this invention to an annular array of piezoelectric crystals. The materials used for the outer and inner lens elements are the same as previously described. An outer lens element 42 has a slightly curved outer surface and an inner surface 44 that is generally circular or parabolic so as to force the acoustic beam of energy at a desired point along the axis 46. The lens element 42 is circular in cross-section and has an annular skirt 48 extending below the surface 44. An outwardly extending flange 50 extends from the annular skirt 48 and rests on a base 52 that supports an array of annular piezoelectric crystals 54 within the annular skirt 48. A plastic nose 56 has a cylindrical opening that abuts against the outer surface of the skirt 48 and is provided with an inner annular shoulder 58 that rests on the top of the flange 50 and an outer annular shoulder. A plastic hollow handle 62 of circular cross-section surrounds the base 52 and is provided with an annular ridge 64 that fits around the outside of the annular shoulder 60 of the nose 56. Pins 66 and 68 may be force-fit in holes, not shown, that extend through the ridge 64 and into the shoulder 60. The inner lens element 70 is formed during assembly by pressing a potting compound between a circular metal shield 72 that is in electrical contact with the tops of the crystals 54 and the inner surface 44 of the outer lens element 42.

Assembly is the same as previously described. The outer lens element is inserted in the nose 56 so that the upper surface of its flange 50 rests on the shoulder 58. The inside of the outer lens element 42 is then filled with the potting compound that forms the inner lens element 70. The base 52 with the array of annular crystals 54 attached thereto is mounted in the position shown so that the flange 50 rests on the top of the base 52. The hollow handle 62 is mounted in the position shown in FIG. 4A and the pins 66 and 68 are inserted.

What is claimed is:

1. A transducer for use in transmitting acoustic signals into a body of a patient to be examined and translating reflections thereof into electrical signals, comprising a base, an array of crystals mounted on said base, a metal shield covering the ends of the said crystals remote from said base and in electrical contact therewith, a first lens element comprised of electrically insulating material having an acoustic impedance approximating that of the tissue under examination and an acoustic propagation velocity greater than that of the tissue under examination, said first element having a concave inner surface and an outer surface, said surfaces being shaped so that parallel rays approaching said inner surface are focussed on the other side of said outer surface, means for mounting said first lens element with its concave inner surface facing said metal shield and on the side of said shield opposite said crystals, and a second lens element comprised of electrically insulating material contained between the inner concave surface of said first lens element and said metal shield, said latter material having an acoustic impedance and propagation velocity approximating those of the tissue under examination.

2. A transducer as set forth in claim 1 in which said first lens element is comprised of rubber modified polymethylpentene.

3. A transducer as set forth in claim 1 in which said first lens element is comprised of rubber modified polyethylene.

4. A transducer as set forth in claim 1 in which said first lens element is comprised of rubber modified polypropylene.

5. A transducer as set forth in any of claims 1 through 4 in which said second lens element is comprised of urethane potting material.

* * * * *